(12) United States Patent
Magno

(10) Patent No.: US 11,382,684 B2
(45) Date of Patent: Jul. 12, 2022

(54) ELECTRODE BLADE FOR SHAVERS

(71) Applicant: Gyrus ACMI, Inc., Southborough, MA (US)

(72) Inventor: Joey Magno, Cordova, TN (US)

(73) Assignee: Gyrus Acmi, Inc., Westborough, MA (US)

( * ) Notice: Subject to any disclaimer, the term of this patent is extended or adjusted under 35 U.S.C. 154(b) by 674 days.

(21) Appl. No.: 15/936,678

(22) Filed: Mar. 27, 2018

(65) Prior Publication Data

US 2019/0298436 A1     Oct. 3, 2019

(51) Int. Cl.
| A61B 18/14 | (2006.01) |
| A61B 18/04 | (2006.01) |
| A61B 18/12 | (2006.01) |
| A61B 18/00 | (2006.01) |

(52) U.S. Cl.
CPC ........ *A61B 18/1402* (2013.01); *A61B 18/042* (2013.01); *A61B 18/1206* (2013.01); *A61B 18/148* (2013.01); *A61B 2018/00029* (2013.01); *A61B 2018/00208* (2013.01); *A61B 2018/00327* (2013.01); *A61B 2018/00577* (2013.01); *A61B 2018/00589* (2013.01); *A61B 2018/00601* (2013.01); *A61B 2018/00607* (2013.01); *A61B 2018/00916* (2013.01);
(Continued)

(58) Field of Classification Search
CPC .............. A61B 18/042; A61B 18/1206; A61B 18/1402; A61B 18/148; A61B 2018/00029; A61B 2018/00208; A61B 2018/00327; A61B 2018/00577; A61B 2018/00589; A61B 2018/00601; A61B 2018/00607; A61B 2018/00916; A61B 2018/126; A61B 2018/1412; A61B 2018/1472; A61B 2218/002; A61B 2218/007
See application file for complete search history.

(56) References Cited

U.S. PATENT DOCUMENTS 4,034,761 A * 7/1977 Prater ................ A61B 18/1402
606/42
5,437,665 A    8/1995 Munro
(Continued)

FOREIGN PATENT DOCUMENTS

CN    110301975 A    10/2019
DE    102017011054 A1    5/2019
(Continued)

OTHER PUBLICATIONS

"Straightshot M4 Microdebrider". Retrieved 2018 from ¬¬http://www.medtronic.com/us-en/healthcare-professionals/products/ear-nose-throat/powered-ent-instruments/powered-ent-instruments/handpieces-accessories.html, 1 page.
(Continued)

*Primary Examiner* — Michael F Peffley
*Assistant Examiner* — Amanda L Zink
(74) *Attorney, Agent, or Firm* — Schwegman Lundberg & Woessner, P.A.

(57) ABSTRACT

Disclosed herein is a medical device. The medical device includes an outer tubular member, an irrigation line, and a bipolar electroblade. The irrigation line is configured to be received within the outer tubular member. The bipolar electroblade is configured to be capable of rotating or oscillating within the outer tubular member.

22 Claims, 6 Drawing Sheets

(52) U.S. Cl.
CPC . *A61B 2018/126* (2013.01); *A61B 2018/1412* (2013.01); *A61B 2018/1472* (2013.01); *A61B 2218/007* (2013.01)

(56) References Cited

U.S. PATENT DOCUMENTS

| | | | | |
|---|---|---|---|---|
| 5,484,435 | A * | 1/1996 | Fleenor | A61B 18/1442 606/46 |
| 6,193,715 | B1 * | 2/2001 | Wrublewski | A61B 18/1402 604/22 |
| 6,610,059 | B1 * | 8/2003 | West, Jr. | A61B 17/32002 606/41 |
| 7,150,747 | B1 * | 12/2006 | McDonald | A61B 18/148 606/45 |
| 7,566,333 | B2 * | 7/2009 | Van Wyk | A61B 18/1485 606/41 |
| 7,699,846 | B2 * | 4/2010 | Ryan | A61B 17/32002 606/50 |
| 9,427,249 | B2 * | 8/2016 | Robertson | A61B 17/320068 |
| 9,427,279 | B2 * | 8/2016 | Muniz-Medina | A61B 17/32002 |
| 9,504,521 | B2 * | 11/2016 | Deutmeyer | A61B 17/32002 |
| 10,179,023 | B2 * | 1/2019 | Ladtkow | A61B 18/1482 |
| 10,342,595 | B2 * | 7/2019 | Hancock | A61B 18/1815 |
| 10,376,302 | B2 * | 8/2019 | Prisco | A61B 18/14 |
| 10,653,478 | B2 * | 5/2020 | Bloom | A61B 18/1445 |
| 10,675,087 | B2 * | 6/2020 | Truckai | A61B 18/1492 |
| 10,813,686 | B2 * | 10/2020 | Bloom | A61B 18/1485 |
| 2002/0013579 | A1 * | 1/2002 | Silvestrini | A61F 9/013 606/32 |
| 2003/0009164 | A1 * | 1/2003 | Woloszko | A61B 18/1492 606/41 |
| 2003/0060862 | A1 * | 3/2003 | Goble | A61B 17/32002 607/96 |
| 2004/0006339 | A1 | 1/2004 | Underwood et al. | |
| 2014/0276795 | A1 * | 9/2014 | Batchelor | A61B 18/1233 606/42 |
| 2014/0276813 | A1 * | 9/2014 | Gambrell | A61B 18/1482 606/49 |
| 2015/0173825 | A1 * | 6/2015 | Bloom | A61B 17/32002 606/50 |
| 2016/0235468 | A1 | 8/2016 | Prisco et al. | |
| 2016/0235469 | A1 * | 8/2016 | Prisco | A61B 18/1485 |
| 2016/0346037 | A1 * | 12/2016 | Truckai | A61B 18/1492 |
| 2016/0353978 | A1 | 12/2016 | Miller et al. | |
| 2017/0252099 | A1 * | 9/2017 | Orczy-Timko | A61B 18/1482 |
| 2019/0059983 | A1 * | 2/2019 | Germain | A61B 17/1615 |

FOREIGN PATENT DOCUMENTS

| | | |
|---|---|---|
| EP | 2863822 A1 | 4/2015 |
| EP | 3545891 A2 | 10/2019 |
| JP | 2009542371 A | 12/2009 |
| JP | 2019171030 A | 10/2019 |

OTHER PUBLICATIONS

"Straightshot M5 Microdebrider". Retrieved 2018 from http://www.medtronic.com/for-healthcare-professionals/business-unit-landing-Page/straightshot-m5-30k-burs/index.htm, 1 page.

"Multidebrider Diego Elite". Retrieved 2018, from ¬¬-http://medical.olympusamerica.com/products/debrider/diego%C2%AE-elite, 2 pages.

"ESSx Microdebrider". 2007. Retrieved 2018 from https://nse.stryker.com/wp-content/uploads/2016/09/ESSx-Microdebrider-brochure.pdf, 2 pages.

"CoolCut Shaver Blades and Burrs—Specialty Series", Arthrex, 2018, 4 pages.

"A clear advantage in uterine tissue removal", Smith&Nephew Truclear System, 2015, 8 pages.

"Myosure Hysteroscopic Tissue Removal System—Instructions for Use", Hologic, Inc., 2015-2016, 5 pages.

"European Application Serial No. 19162704.1, Extended European Search Report dated Nov. 25, 2019", 8 pgs.

"European Application Serial No. 19162704.1, Partial European Search Report dated Jul. 11, 2019", 7 pgs.

"European Application Serial No. 19162704.1, Response filed Jun. 8, 2020 to Extended European Search Report dated Nov. 25, 2019", 6 pgs.

"Japanese Application Serial No. 2019-038400, Office Action dated Nov. 24, 2020", w/ English Translation, 6 pgs.

"Japanese Application Serial No. 2019-038400, Response filed Mar. 26, 2021 to Office Action dated Nov. 24, 2020", w/English Claims.

"Japanese Application Serial No. 2019-38400, Examiners Decision of Final Refusal dated Jun. 7, 2021", 6 pgs.

* cited by examiner

ELECTRODE BLADE FOR SHAVERS

BACKGROUND

Field of the Invention

The invention relates to a medical device and more specifically relates to a medical shaver device having an electrode blade.

Brief Description of Prior Developments

Various conventional products (such as from Truclear [Smith & Nephew], Myosure [Hologic], and M4/M5 [Medtronic]) provide shavers, microdebriders, and tissue removal devices having mechanical cutting methods. For example, typical blades for conventional devices have a stationary outer blade that has the window opening and an inner blade that oscillates multiple turns in one direction, pauses, and then reverses in the other direction. These occur at 3000 to 5000 RPM. Negative suction pressure will be present in the cutting window to extract any tissues that have been resected from the patient. However, these mechanical cutting methods can result in excessive bleeding during and/or after the procedure which can add to patient recovery time.

For example, some conventional configurations participate in functional endoscopic sinus surgery (FESS) that diagnose and treat diseases of the nose and sinus using endoscopes and CT scans with cutting instruments, powered debriders with suction where the sinus openings will be enlarged and anything blocking the sinus, such as swollen mucosa, bone, or polyps are resected.

One conventional configuration from Smith & Nephew, for example, provides a tissue removal device for hysterectomy, which as has three mechanical blade styles which are very similar to the ENT blades that oscillate during operation to resect hard to reach tissues in the upper inside wall of the fundus of the uterus.

Another conventional configuration (Ultra plus), provides three blades and utilizes a reciprocating inner blade is used to resect larger and harder tissues. Additionally, Smith and Nephew has similar debriders for arthroscopy, which have more mechanical cutting methods.

As mentioned above, generally with mechanical methods of cutting, there is a risk of excessive bleeding, either during or up to two weeks after the operation. It is a huge inconvenience and affects the patient's recovery time. Additionally, about 2% of patients may need a second operation to control bleeding, readmission to hospital, or a blood transfusion if heavy bleeding occurs.

Accordingly, as the conventional designs generally result in various disadvantages (as described above), there is a need to provide improved and reliable product configurations.

SUMMARY

In accordance with one aspect of the invention, a medical device is disclosed. The medical device includes an outer tubular member, an irrigation line, and a bipolar electroblade. The irrigation line is configured to be received within the outer tubular member. The bipolar electroblade is configured to be capable of rotating or oscillating within the outer tubular member.

In accordance with another aspect of the invention, a medical device is disclosed. The medical device includes an outer tubular member, an irrigation line, and a bipolar plasma dome. The irrigation line is configured to be received within the outer tubular member. The bipolar plasma dome is configured to be disposed at a distal end of the medical device.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
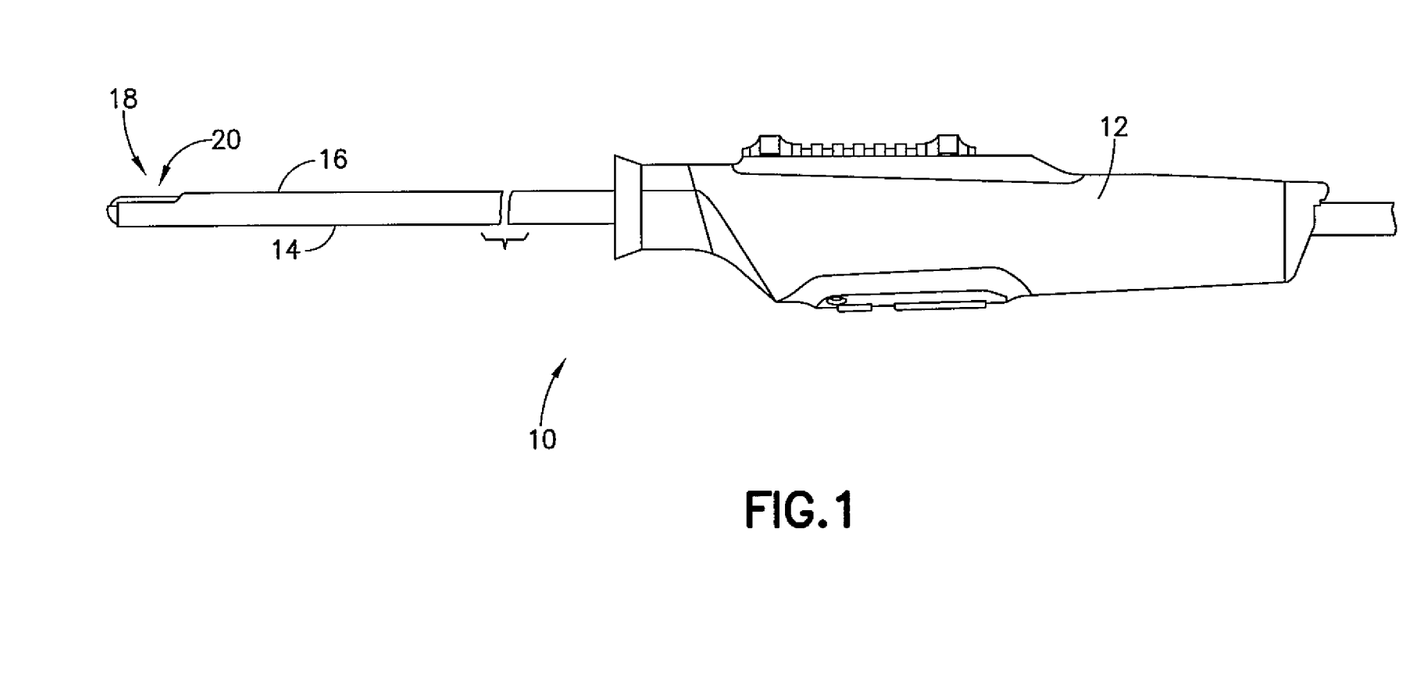
FIG. 1 is a side view of a medical device incorporating features of the invention.

Referring to FIG. 1, there is shown a perspective view of a medical device 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

In the embodiment shown in FIG. 1, the medical device (or cutting device) 10 includes a handpiece 12 and a blade assembly 14. The blade assembly 14 comprises an outer sheath 16 having a window opening 18. The outer sheath comprises a general tubular shape. The blade assembly 14 further comprises an inner blade configuration having an "electroblade" 20 instead of mechanical inner blades. The "electroblade" 20 comprises saline electrodes that are configured to burn through tissue and act as a cutting blade and/or a coagulating blade.

The window opening 18 of the outer sheath 16 is sized and shaped to expose the cutting member of the "electroblade" 20. The sheath 16 (which may be non-metallic, for example) is generally stationary all the time. The sheath 16 also generally determines the commercial size of the "electroblade" 20. The sheath 16 also provides a bearing surface for the inner blade assembly to keep it aligned at the center (discussed further below).

Figure 2:
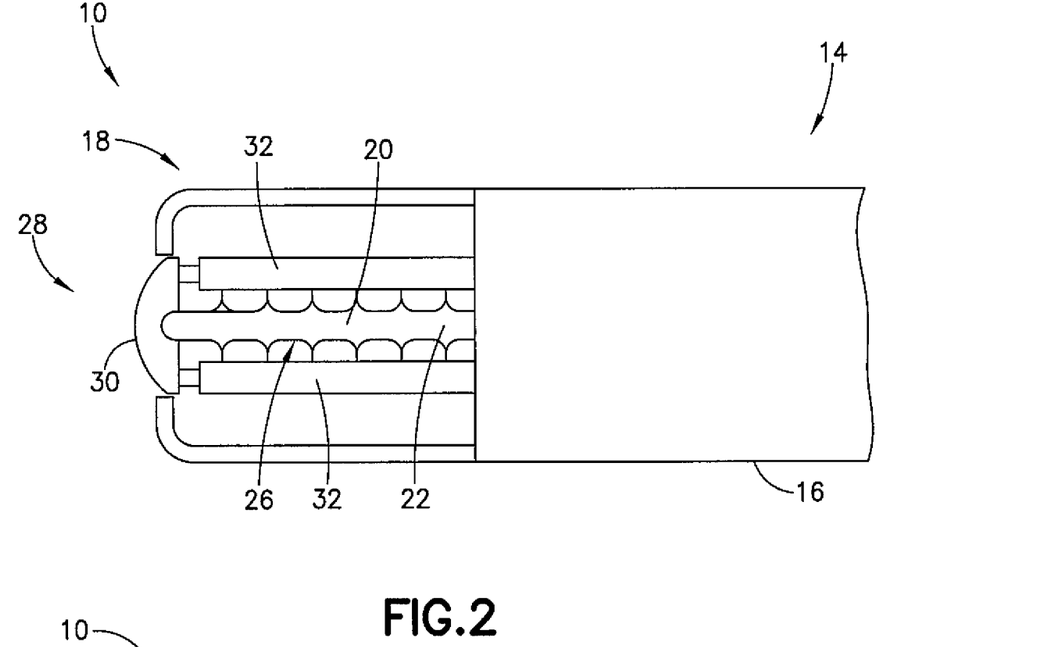
FIG. 2 is an enlarged view of a distal end of the medical device shown in FIG. 1.
Figure 3:
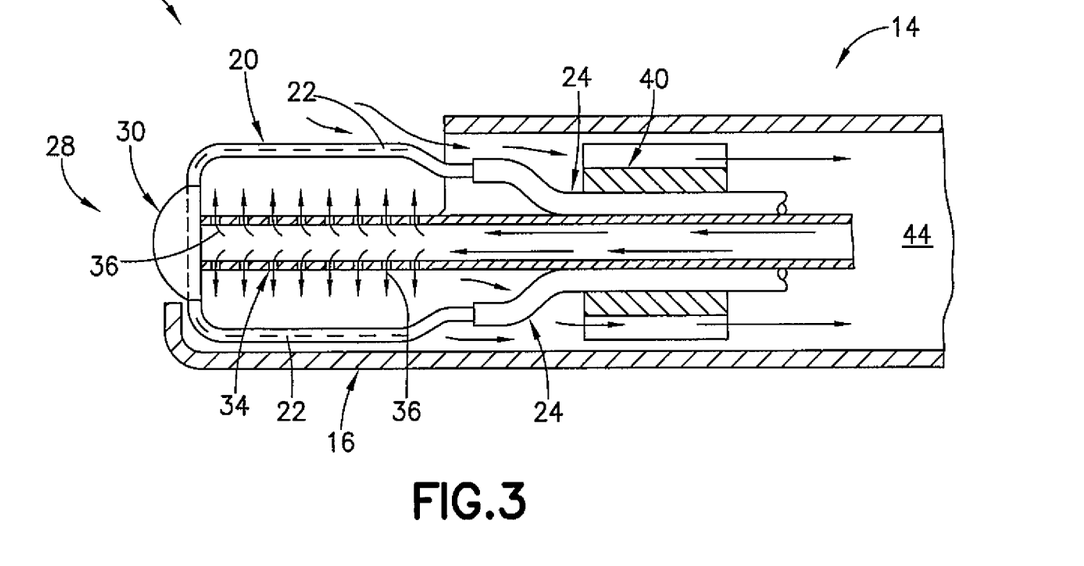
FIG. 3 is a section view of the distal end of the medical device shown in FIG. 1.
Figure 4:
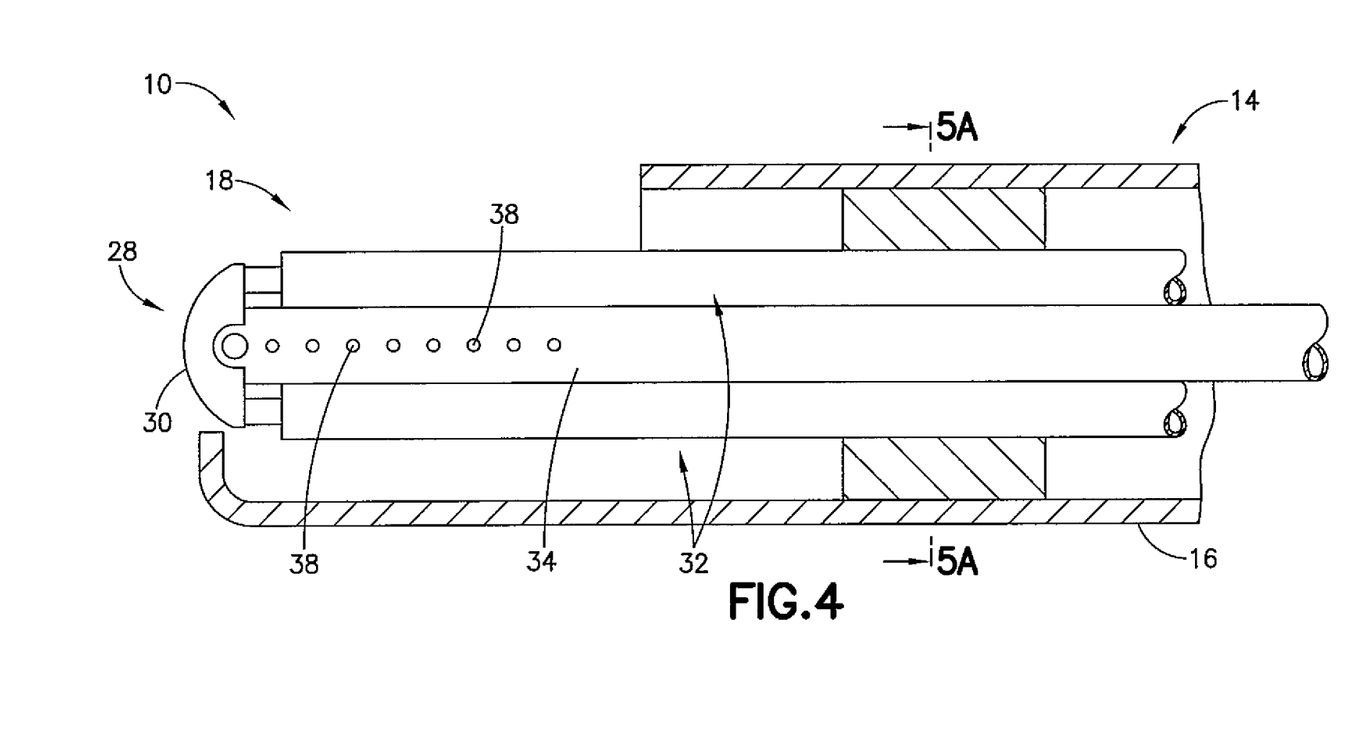
FIG. 4 is another section view of the distal end of the medical device shown in FIG. 1.

Referring now also to FIGS. 2-4, enlarged views of the inner blade configuration is shown. According to various exemplary embodiments of the invention, the rotating "electroblade" 20 is "side cutting electroblade" edge form that is made of a loop cutting wire 22 (connected to electroblade bipolar supply lines 24). According to various alternate embodiments, the "electroblade" 20 may further comprise formed serrated teeth edges 26 on both sides of the blades (providing a serrated electroblade tooth profile).

According to various exemplary embodiments, a distal end 28 of the medical device 10 also has a dome structure 30 similar to a "plasma button" that can ablate or coagulate depending on the power level selected on a bipolar control setting. This dome "plasma button" 30 can have separate bipolar lines 32 for power supply.

According to various exemplary embodiments, the inner blade loop cutting wire 22 and the plasma button 30 must be covered or irrigated with a narrow band stream of saline fluid (from a saline irrigation supply tube 34) in order to avail of its electrical conducting properties. The stream of saline fluid 36 is discharged from openings 38 of the saline irrigation supply tube 34 every time the electrode blade 20 or plasma button 30 is activated. The nozzles (or openings) 38 for this irrigation supply rotates respectively and always directed towards the electrode blade 20 or plasma button 30 when energized.

Figure 5A:
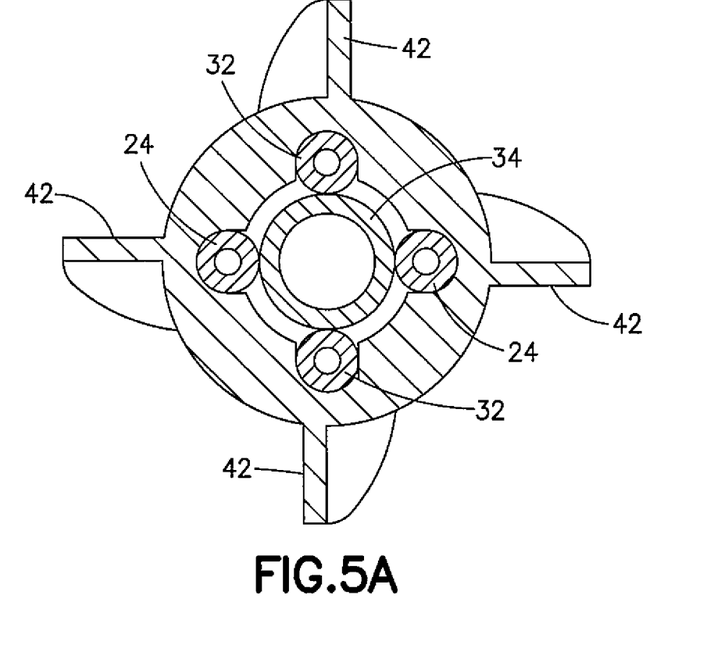
FIG. 5A is a cross section view taken from the corresponding lines shown in FIG. 4.
Figure 5B:
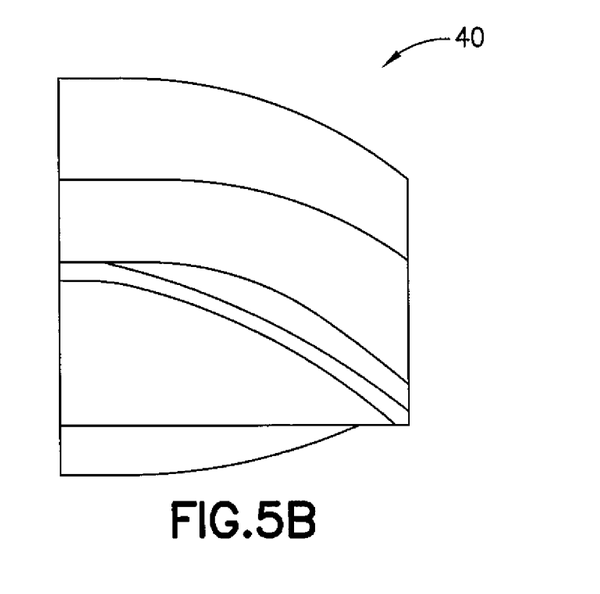
FIG. 5B is a view of an inner blade bearing of the medical device shown in FIG. 1.

Referring now also to FIG. 5A, the inner blade is being held at the center by a floating (or inner blade) bearing 40 (also see FIG. 3). This bearing is fitted snugly with the bipolar lines 24, 32 and the irrigation tube 34 and it has 3-4 ribs 42 that work as impellers or fan blades to help the suction negative pressure push and extract the debris to the suction line/path. Depending on the length of the blade, there may be 2 to 3 or more of these bearings in place to keep the inner blade assembly centered. FIG. 5B also shows an alternate side view of the inner blade bearing 40.

Figure 6A:
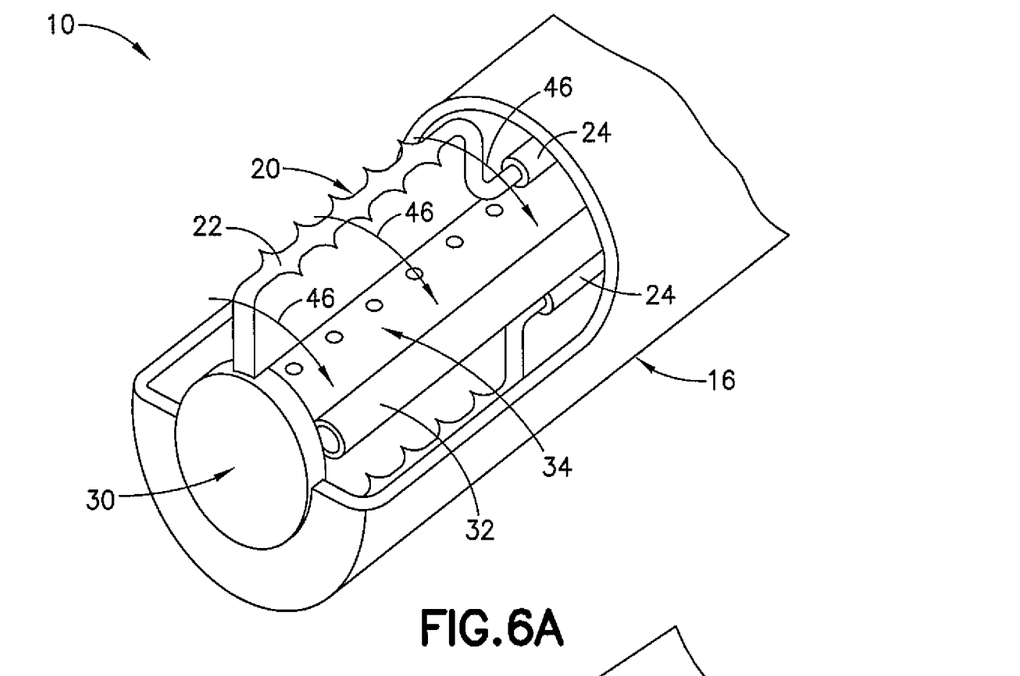
FIG. 6A is a perspective view of the distal end of the medical device shown in FIG. 1.
Figure 6B:
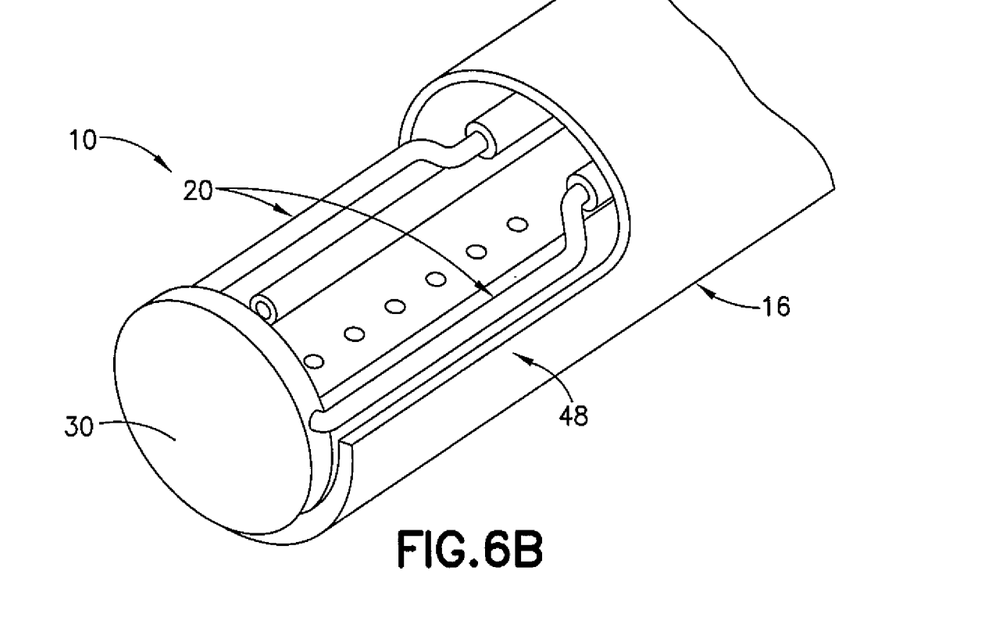
FIG. 6B is a perspective view of a distal end of an alternate embodiment of the medical device incorporating features of the invention.

According to various exemplary embodiments, the medical device 10 generally operates similar to traditional mechanical microdebriders. For example, and referring now also to FIG. 6A, every time the device is energized, a drive motor from the hand piece will rotate the electroblade 20, the plasma dome 30, irrigation tube 34 (and corresponding bipolar supply lines 24, 32) of the inner blade assembly in single directional mode at a preset RPM (see direction of rotation at arrows 46). One difference is, instead of mechanical cutting action, an energized "electroblade" 20 with the inner loop cutting wire 22 acts as a cutting blade and "burns" through the tissue to be resected. This method coagulates the tissue resected and prevents bleeding of exposed vascular vessels. Debris and other materials such as irrigation fluid are extracted through the suction path 44 of the inner blade (see FIG. 3). If additional coagulation is needed, the dome "plasma button" 30 can be activated separately to perform such function. Referring now also to FIG. 6B, if the plasma dome 30 is unable to reach the area to be coagulated, the electroblade 20 can be operated by just energizing the bipolar energy 48 alone that is positioned on its sides fixed and non-rotating in order for the surgeon to perform coagulating effect on the tissue. Moreover, in alternate embodiments, the plasma dome 30 can be enlarged (see FIG. 6B) to cover a larger area that can be coagulated. This will also simplify the tip design of the outer sheath 16 by leaving the end open instead of having a drawn tube or welding operation to close the ends. Additionally, in other alternate embodiments, the plasma dome 30 can be configured to be stationary or can be configured to be rotated by a drive motor.

Figure 7:
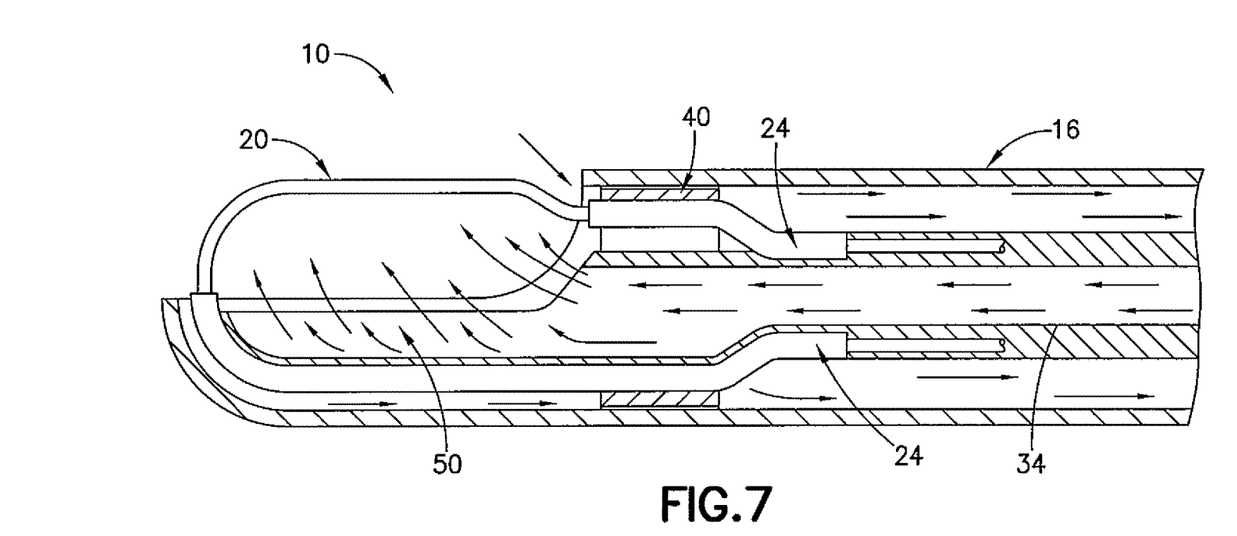
FIG. 7 is a section view of a distal end of another alternate embodiment of the medical device incorporating features of the invention.
Figure 8:
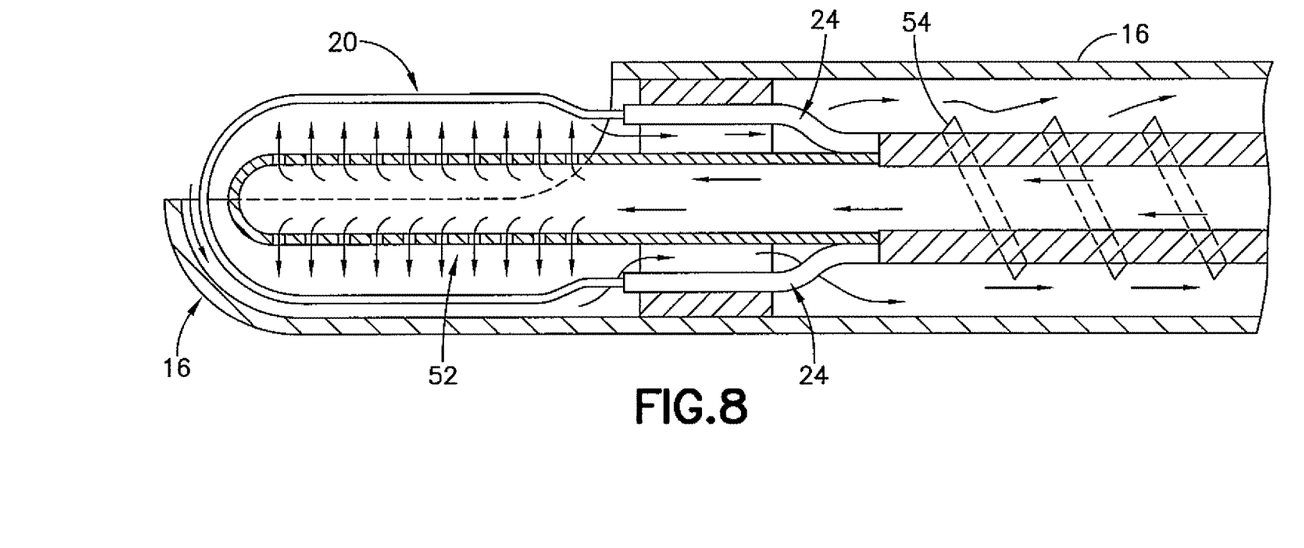
FIG. 8 is a section view of a distal end of another alternate embodiment of the medical device incorporating features of the invention.

According to various alternate examples of the invention, the medical device can also be provided without a plasma dome. For example, referring now also to FIG. 7, the electroblade 20 may be configured to be a single sided cutter that can operate on oscillating or one direction rotation. Or, it can be provided as one continuous loop of electro blade as shown in FIG. 8. Both embodiments of FIGS. 7 and 8 utilize the same principle of having a directed stream of saline whenever the cutting operation is energized to have bipolar conductivity effective through the tissue being resected. For example, arrow 50 in FIG. 7 illustrates where a narrow band spray of saline fluid is directed at the entire height of the electroblade, and arrow 52 in FIG. 8 illustrates where a narrow band spray of saline fluid is directed on the plane of the electroblade. Additionally, the inner blade assembly with the irrigation tube 34 can have a fluted (or screw configuration) outside diameter 54 that can act as an auger to push the debris out to the suction path.

Technical effects of any one or more of the exemplary embodiments provide significant advantages over conventional configurations by eliminating the need for mechanical debriding using metallic blade cutters. Instead of mechanical inner blades, the various exemplary embodiments of the invention use saline electrodes that make bloodless treatment possible and reduces procedure time compared to other conventional methods. The electrodes deliver clean and precise cutting and simultaneous coagulation which is beneficial in FESS procedures. Another procedure where this will be most beneficial is in tonsil and adenoid. Since these are all mucosal and have many vascular tissues, current mechanical cutting methods cause severe bleeding for the patient. Surgeons always want a coagulating effect so that the procedure can done quicker, by cutting and coagulating the tissues at the same time (as with the various exemplary embodiments of the invention). Additionally, patients will benefit from these features as it will minimize the amount of packing that needs to be applied to control bleeding after the procedure and reduce the amount of recovery time.

With regards to equipment design, various exemplary embodiments of the invention provide for simplified motor drive control units as it may not require high RPMs, or high torque requirements as compared to mechanical methods due to shearing force required with mechanical blades, and therefore lower the cost of the handpiece unit.

Various exemplary embodiments of the invention provide an end product that will be represented by an "Electroblade" incorporated with a disposable handpiece similar to MyoSure for GYN or a stand-alone disposable blade attached to a reusable handpiece similar to Diego Elite or Medtronic M4/MS for ENT operations.

Various exemplary embodiments of the invention provide a bipolar electrode blade that can be operated with the same oscillating action as described above or may be designed to have an operating mode to run in one direction. To activate conductivity, the electrode blade will be provided with steady stream of irrigating saline fluid whenever the device is energized. Additionally, a suction path can be provided to extract tissues, debris and smoke that will occur during resecting operation.

It should be noted that in addition to the procedures listed above, the various exemplary embodiments of the inventions may also be applicable in other shaver operations such as in Uro/Gyn or in Arthroscopy.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a medical device comprising: an outer tubular member; an irrigation line configured to be received within the outer tubular member; and a bipolar electroblade configured to be capable of rotating or oscillating within the outer tubular member.

A medical device as above, further comprising a bipolar plasma dome configured to be disposed at a distal end of the medical device.

A medical device as above, wherein the bipolar electroblade comprises saline electrodes configured to burn through tissue.

A medical device as above, wherein the bipolar electroblade comprises serrated teeth.

A medical device as above, wherein the outer tubular member comprises a window opening proximate a distal end of the medical device.

A medical device as above, wherein the bipolar electroblade is disposed within the window opening.

A medical device as above, wherein the bipolar electroblade comprises a loop cutting wire connected to an electroblade bipolar supply line.

A medical device as above, wherein the electroblade bipolar supply line is adjacent the irrigation line.

A medical device as above, wherein the irrigation line has a fluted outside diameter.

A medical device as above, wherein the medical device is configured such that the bipolar electroblade is always provided with a steady stream and a narrow band of saline fluid that follows the bipolar electroblade when activated as it rotates.

In another exemplary embodiment, a medical device comprising: an outer tubular member; an irrigation line configured to be received within the outer tubular member; and a bipolar plasma dome configured to be disposed at a distal end of the medical device.

A medical device as above, further comprising a bipolar electroblade configured to be capable of rotating or oscillating within the outer tubular member.

A medical device as above, wherein the bipolar electroblade comprises serrated teeth.

A medical device as above, wherein the bipolar electroblade comprises saline electrodes configured to burn through tissue.

A medical device as above, wherein the bipolar electroblade is disposed within a window opening of the outer tubular member.

A medical device as above, wherein the bipolar electroblade comprises a loop cutting wire connected to an electroblade bipolar supply line.

A medical device as above, wherein the medical device is configured such that the bipolar electroblade is always provided with a steady stream and a narrow band of saline fluid that follows the bipolar electroblade when activated as it rotates.

A medical device as above, wherein the bipolar plasma dome is connected to a plasma dome bipolar supply line.

A medical device as above, wherein the plasma dome bipolar supply line is adjacent the irrigation line.

A medical device as above, wherein the irrigation line has a fluted outside diameter.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A medical device comprising:
   an outer tubular member;
   an irrigation line configured to be received within the outer tubular member; and
   a bipolar electroblade configured to be capable of rotating within the outer tubular member in one or more complete revolutions, the bipolar electroblade including a plurality of electrodes that, when energized, cause the bipolar electroblade to burn through tissue and act as a cutting blade;
   wherein the irrigation line is configured to rotate together with the bipolar electroblade such that fluid outlets of the irrigation line are directed towards the bipolar electroblade during operation of the device.

2. The medical device of claim 1 further comprising a bipolar plasma dome configured to be disposed at a distal end of the medical device.

3. The medical device of claim 1 wherein the electrodes of the bipolar electroblade comprise saline electrodes.

4. The medical device of claim 1 wherein the bipolar electroblade comprises serrated teeth.

5. The medical device of claim 1 wherein the outer tubular member comprises a window opening proximate a distal end of the medical device.

6. The medical device of claim 5 wherein the bipolar electroblade is disposed within the window opening.

7. The medical device of claim 1 wherein the bipolar electroblade comprises a loop cutting wire connected to an electroblade bipolar supply line.

8. The medical device of claim 7 wherein the electroblade bipolar supply line is adjacent the irrigation line.

9. The medical device of claim 1 wherein the irrigation line has a fluted outside diameter.

10. The medical device of claim 1 wherein the fluid outlets of the irrigation line are configured to provide a steady stream and a narrow band of saline fluid.

11. A medical device comprising:
    an outer tubular member;
    an irrigation line configured to be received within the outer tubular member;
    a bipolar plasma dome configured to be disposed at a distal end of the medical device; and
    a bipolar electroblade configured to rotate or oscillate within the outer tubular member, wherein the bipolar electroblade is disposed within a window opening of the outer tubular member, and wherein the irrigation line is configured to rotate or oscillate together with the bipolar electroblade such that fluid outlets of the irrigation line are directed towards the bipolar electroblade during operation of the device.

12. A medical device comprising:
    an outer tubular member;
    an irrigation line configured to be received within the outer tubular member;
    a bipolar plasma dome configured to be disposed at a distal end of the medical device; and a bipolar electroblade configured to rotate or oscillate within the outer tubular member, wherein the bipolar electroblade is disposed within a window opening of the outer tubular member, and wherein the irrigation line is configured to rotate or oscillate together with the bipolar electroblade such that fluid outlets of the irrigation line are always directed towards the bipolar electroblade during operation of the device.

13. The medical device of claim 12 wherein the bipolar electroblade comprises serrated teeth.

14. The medical device of claim 12 wherein the bipolar electroblade comprises saline electrodes configured to burn through tissue.

15. The medical device of claim 12 wherein the bipolar electroblade comprises a loop cutting wire connected to an electroblade bipolar supply line.

16. The medical device of claim 12 wherein the medical device is configured such that the bipolar electroblade is always provided with a steady stream and a narrow band of saline fluid that follows the bipolar electroblade when activated as it rotates.

17. The medical device of claim 12 wherein the bipolar plasma dome is connected to a plasma dome bipolar supply line.

18. The medical device of claim 17 wherein the plasma dome bipolar supply line is adjacent the irrigation line.

19. The medical device of claim 12 wherein the irrigation line has a fluted outside diameter.

20. The medical device of claim 12, wherein the fluid outlets in the irrigation line comprise nozzles.

21. The medical device of claim 12, wherein the bipolar plasma dome is configured to rotate or oscillate together with the bipolar electroblade.

22. A medical device comprising:
an outer tubular member;
an irrigation line configured to be received within the outer tubular member; and
a bipolar electroblade configured to rotate within the outer tubular member in one or more complete revolutions;
wherein the irrigation line is configured to rotate together with the bipolar electroblade such that fluid outlets of the irrigation line are directed towards the bipolar electroblade during operation of the device.

* * * * *

UNITED STATES PATENT AND TRADEMARK OFFICE
CERTIFICATE OF CORRECTION

PATENT NO. : 11,382,684 B2
APPLICATION NO. : 15/936678
DATED : July 12, 2022
INVENTOR(S) : Joey Magno It is certified that error appears in the above-identified patent and that said Letters Patent is hereby corrected as shown below:

In the Claims

In Column 6, Lines 48-61, in Claim 11, delete "A medical device comprising:
an outer tubular member;
an irrigation line configured to be received within the outer tubular member;
a bipolar plasma dome configured to be disposed at a distal end of the medical device; and
a bipolar electroblade configured to rotate or oscillate within the outer tubular member, wherein the bipolar electroblade is disposed within a window opening of the outer tubular member, and wherein the irrigation line is configured to rotate or oscillate together with the bipolar electroblade such that fluid outlets of the irrigation line are directed towards the bipolar electroblade during operation of the device." and insert --The medical device of claim 1 wherein when the electrodes of the bipolar electroblade are energized, the bipolar electroblade simultaneously cuts and coagulates the tissue.-- therefor In Column 7, Line 7, in Claim 12, after "are", delete "always"

Signed and Sealed this
Twenty-first Day of March, 2023

Katherine Kelly Vidal
*Director of the United States Patent and Trademark Office*